United States Patent
Kobayashi et al.

(10) Patent No.: US 6,989,356 B2
(45) Date of Patent: Jan. 24, 2006

(54) PARTIALLY-FLUORINATED-ALKYL COMPOUND, LUBRICANT COMPRISING THE COMPOUND, AND RECORDING MEDIUM USING THE LUBRICANT

(75) Inventors: Ken Kobayashi, Kanagawa (JP);
Takahiro Kamei, Kanagawa (JP);
Noriyuki Kishii, Kanagawa (JP);
Kenichi Kurihara, Kanagawa (JP);
Yutaka Iwamoto, Kanagawa (JP);
Hisanori Tsuboi, Kanagawa (JP)

(73) Assignee: Sony Corp., Tokyo (JP)

( * ) Notice: Subject to any disclaimer, the term of this patent is extended or adjusted under 35 U.S.C. 154(b) by 337 days.

(21) Appl. No.: 10/408,904

(22) Filed: Apr. 8, 2003

(65) Prior Publication Data

US 2003/0224953 A1    Dec. 4, 2003

(30) Foreign Application Priority Data

Apr. 10, 2002  (JP)  .............................. 2002-107463
Apr. 10, 2002  (JP)  .............................. 2002-107464

(51) Int. Cl.
*C10M 105/50*  (2006.01)
*C07C 69/62*  (2006.01)
*G11B 5/725*  (2006.01)

(52) U.S. Cl. ...................... 508/477; 508/478; 508/483; 508/496; 508/497; 560/190; 560/197; 428/835.6; 428/835.7; 428/900

(58) Field of Classification Search ........ 508/465–499; 560/190, 197; 428/835.6, 835.7
See application file for complete search history.

(56) References Cited

U.S. PATENT DOCUMENTS

| | | | | |
|---|---|---|---|---|
| 5,188,747 A | * | 2/1993 | Kai et al. | 508/482 |
| 5,391,814 A | * | 2/1995 | Kai et al. | 508/478 |
| 5,510,513 A | * | 4/1996 | Kai et al. | 560/197 |
| 5,578,387 A | * | 11/1996 | Kai et al. | 428/694 T |
| 5,604,032 A | * | 2/1997 | Kai et al. | 428/336 |
| 5,679,752 A | * | 10/1997 | Arudi et al. | 526/245 |
| 6,103,677 A | * | 8/2000 | Furutani et al. | 508/465 |
| 6,187,724 B1 | * | 2/2001 | Ikarashi et al. | 508/463 |
| 6,265,060 B1 | * | 7/2001 | Arudi et al. | 428/323 |
| 6,303,227 B1 | * | 10/2001 | Kuwahara et al. | 428/421 |

* cited by examiner

*Primary Examiner*—Ellen M. McAvoy
(74) *Attorney, Agent, or Firm*—Trexler, Bushnell, Giangiorgi, Blackstone & Marr, Ltd.

(57) ABSTRACT

To provide a lubricant for recording medium, which is advantageous not only in that it maintains excellent lubricity under various conditions for use and excellent lubricating effect over a long time, but also in that it can impart excellent transport properties and excellent abrasion resistance as well as excellent durability. For example, when $C_{18}H_{37}$—CH($CH_2COOC_{10}H_6OH$)COORf (wherein Rf represents a saturated or unsaturated partially-fluorinated-alkyl group) is used as a lubricant for magnetic recording medium, there can be obtained a magnetic recording medium having excellent transport properties and excellent abrasion resistance as well as excellent durability.

7 Claims, No Drawings

PARTIALLY-FLUORINATED-ALKYL COMPOUND, LUBRICANT COMPRISING THE COMPOUND, AND RECORDING MEDIUM USING THE LUBRICANT

RELATED APPLICATION DATA

This application claims priority to Japanese Patent Application JP 2002-107463 filed on Apr. 10, 2002 and 2002-107464 filed on Apr. 10, 2002, and the disclosures of these applications are incorporated herein by reference to the extent permitted by law.

BACKGROUND OF THE INVENTION

1. Field of the Invention

The present invention relates to a partially-fluorinated-alkyl compound, a lubricant for recording medium including the partially-fluorinated-alkyl compound, and a recording medium having formed a lubricant layer comprising the lubricant.

2. Description of Related Art

As conventional recording media, for example, magnetic recording media, there have been known so-called metal thin film type magnetic recording media including a magnetic layer which is formed by depositing a ferromagnetic metal material on a nonmagnetic support by using, for example, a vapor deposition process, and so-called coating type magnetic recording media including a magnetic layer which is formed by applying to a nonmagnetic support a magnetic coating composition including very fine magnetic particles and a resin binder. In these conventional magnetic recording media, the magnetic layer has extremely excellent surface smoothness and hence, the substantial contact area of the magnetic layer with a sliding member, such as a magnetic head or a guide roller, is large, namely, the coefficient of friction is large, leading to problems in that a so-called sticking phenomenon due to cohesion is likely to occur and the transport properties and durability of the magnetic recording media are poor.

For solving the problems, various lubricants are studied and, conventionally, it has been attempted to incorporate or apply, as a topcoat, a higher fatty acid or an ester thereof to the magnetic layer in the magnetic recording medium to lower the coefficient of friction.

The magnetic recording medium is used under severe conditions, and therefore the lubricant used in the magnetic recording medium is required to have extremely excellent properties. However, the lubricants conventionally used are currently difficult to meet the requirements.

Specifically, the lubricant used in the magnetic recording medium must meet such requirements: (1) for securing a predetermined lubricating effect when used in cold places, that the lubricant have excellent properties at low temperatures; (2) for removing a problem of the spacing between a magnetic head and the recording medium, that the lubricant applied to the recording medium have an extremely small thickness and exhibit satisfactory lubricating properties; and (3) that the lubricant endure long-time or long-term use and maintain the lubricating effect.

As a lubricant for metal thin film type magnetic recording medium, Japanese Patent Application Laid-Open Specification No. 6-41561 discloses a fluorine-containing alkyl diester of succinic acid represented by the following formula (i):

$$R^1-CH(COOR^2)CH_2COOR^3 \qquad (i)$$

wherein $R^1$ represents an aliphatic alkyl group or an aliphatic alkenyl group; and one of $R^2$ and $R^3$ represents a fluoroalkyl ether group, and another represents a fluoroalkyl group, a fluoroalkenyl group, a fluorophenyl group, an aliphatic alkyl group, or an aliphatic alkenyl group.

SUMMARY OF THE INVENTION

However, the fluorine-containing alkyl diester of succinic acid described above has a problem in that the coefficient of friction is large.

Thus, in the field of recording media, there are problems of the practicalities due to the lack of the ability of the lubricant used, for example, a problem that an output level during the replay is lowered in the shuttle transport test.

In view of the above, the present invention is conceived. It is desirable to provide a compound which is advantageous not only in that it maintains excellent lubricity under various conditions for use and excellent lubricating effect over a long time, but also in that it can impart excellent transport properties and excellent abrasion resistance as well as excellent durability, a lubricant including the compound, and a recording medium using the lubricant.

Specifically, in one aspect of the present invention, there is provided a partially-fluorinated-alkyl compound which is represented by the following formula (1):

wherein R represents a saturated or unsaturated aliphatic hydrocarbon group having 6 to 30 carbon atoms; Rf represents a saturated or unsaturated fluoroalkyl group or hydrocarbon group; and X represents an aromatic ring or heterocyclic group, an aromatic ring or heterocyclic group substituted with a hydroxyl group, an amino group, a carboxyl group, a halogen atom, a hydrocarbon group, or an aromatic ring, or a hydrocarbon group substituted with an aromatic ring or heterocyclic group.

In another aspect of the present invention, there is provided a lubricant for recording medium, wherein the lubricant includes a partially-fluorinated-alkyl compound represented by the following formula (1):

wherein R represents a saturated or unsaturated aliphatic hydrocarbon group having 6 to 30 carbon atoms; Rf represents a saturated or unsaturated fluoroalkyl group or hydrocarbon group; and X represents an aromatic ring or heterocyclic group, an aromatic ring or heterocyclic group substituted with a hydroxyl group, an amino group, a carboxyl group, a halogen atom, a hydrocarbon group, or an aromatic ring, or a hydrocarbon group substituted with an aromatic ring or heterocyclic group.

In still another aspect of the present invention, there is provided a recording medium which includes a support, a recording layer, and a lubricant layer including a lubricant, wherein the recording layer and the lubricant layer are successively formed on the support, wherein the lubricant includes a partially-fluorinated-alkyl compound represented by the following formula (1):

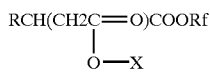
(1)

wherein R represents a saturated or unsaturated aliphatic hydrocarbon group having 6 to 30 carbon atoms; Rf represents a saturated or unsaturated fluoroalkyl group or hydrocarbon group; and X represents an aromatic ring or heterocyclic group, an aromatic ring or heterocyclic group substituted with a hydroxyl group, an amino group, a carboxyl group, a halogen atom, a hydrocarbon group, or an aromatic ring, or a hydrocarbon group substituted with an aromatic ring or heterocyclic group.

In another aspect of the present invention, there is provided a partially-fluorinated-alkyl compound which is represented by the following formula (2):

$$RCH(CH_2COORf)COOX \qquad (2)$$

wherein R represents a saturated or unsaturated aliphatic hydrocarbon group having 6 to 30 carbon atoms; Rf represents a saturated or unsaturated fluoroalkyl group or hydrocarbon group; and X represents an aromatic ring or heterocyclic group, an aromatic ring or heterocyclic group substituted with a hydroxyl group, an amino group, a carboxyl group, a halogen atom, a hydrocarbon group, or an aromatic ring, or a hydrocarbon group substituted with an aromatic ring or heterocyclic group.

In still another aspect of the present invention, there is provided a lubricant for recording medium, wherein the lubricant includes a partially-fluorinated-alkyl compound represented by the following formula (2):

$$RCH(CH_2COORf)COOX \qquad (2)$$

wherein R represents a saturated or unsaturated aliphatic hydrocarbon group having 6 to 30 carbon atoms; Rf represents a saturated or unsaturated fluoroalkyl group or hydrocarbon group; and X represents an aromatic ring or heterocyclic group, an aromatic ring or heterocyclic group substituted with a hydroxyl group, an amino group, a carboxyl group, a halogen atom, a hydrocarbon group, or an aromatic ring, or a hydrocarbon group substituted with an aromatic ring or heterocyclic group.

In still another aspect of the present invention, there is provided a recording medium which includes a support, a recording layer, and a lubricant layer including a lubricant, wherein the recording layer and the lubricant layer are successively formed on the support, wherein the lubricant includes a partially-fluorinated-alkyl compound represented by the following formula (2):

$$RCH(CH_2COORf)COOX \qquad (2)$$

wherein R represents a saturated or unsaturated aliphatic hydrocarbon group having 6 to 30 carbon atoms; Rf represents a saturated or unsaturated fluoroalkyl group or hydrocarbon group; and X represents an aromatic ring or heterocyclic group, an aromatic ring or heterocyclic group substituted with a hydroxyl group, an amino group, a carboxyl group, a halogen atom, a hydrocarbon group, or an aromatic ring, or a hydrocarbon group substituted with an aromatic ring or heterocyclic group.

The partially-fluorinated-alkyl compound of the present invention is a novel substance, and, when the compound is used as a lubricant for recording medium, especially for magnetic recording medium, the compound is advantageous not only in that it maintains excellent lubricity under various conditions for use and excellent lubricating effect over a long time, but also in that it can impart to the recording medium excellent transport properties and excellent abrasion resistance as well as excellent durability.

DESCRIPTION OF THE PREFERRED EMBODIMENTS

Hereinbelow, the compound of the present invention will be described, taking as an example the case where the compound is used as a lubricant for magnetic recording medium.

In the partially-fluorinated-alkyl compound of the present invention, R represents a saturated or unsaturated aliphatic hydrocarbon group having 6 to 30 carbon atoms, preferably 8 to 20 carbon atoms. When the carbon atom number of R is less than 6 or more than 30, the solubility of the compound in an organic solvent is too low, making it impossible to form a film of a lubricant layer using an organic solvent on, for example, a carbon film layer.

First Embodiment

The partially-fluorinated-alkyl compound according to a first embodiment of the present invention may be synthesized, for example, as follows.

First, a succinic acid derivative having the substituent R in formula (1) and an alcohol compound having the fluoroalkyl group (Rf) in formula (1) are mixed together and heated to 120° C. to effect a reaction, and then, impurities and the remaining unnecessary substances are removed from the resultant reaction mixture by washing with an organic solvent or an inorganic solvent, extraction using a separatory funnel, or purification by column chromatography to obtain a partially-fluorinated-alkyl monoester monocarboxylic acid compound purified. Then, the obtained partially-fluorinated-alkyl monoester monocarboxylic acid compound and a hydroxyl compound having the substituent X in formula (1) are subjected to esterification so that one hydroxyl group in the hydroxyl compound having the substituent X is reacted with one carboxyl group in the partially-fluorinated-alkyl monoester monocarboxylic acid compound to form an ester linkage, followed by purification, thus obtaining a partially-fluorinated-alkyl compound.

In the esterification, a method can be employed in which the carboxyl group in the partially-fluorinated-alkyl monoester monocarboxylic acid compound is preliminarily treated with, e.g., thionyl chloride to form an acid chloride, and then reacted with the hydroxyl group in the hydroxyl compound having the substituent X.

As mentioned above, the partially-fluorinated-alkyl compound of the present invention can be advantageously used as a lubricant for recording medium, especially for magnetic recording medium. If desired, various additives, for example, a rust preventing agent can be added to the lubricant. As a rust preventing agent, one which has conventionally been used for magnetic recording medium can be used, and examples include phenols, naphthols, quinones, heterocyclic compounds containing a nitrogen atom, heterocyclic compounds containing an oxygen atom, and heterocyclic compounds containing a sulfur atom.

The recording medium of the present invention includes a lubricant layer including the above lubricant. For example, when the recording medium of the present invention is a magnetic recording medium, it can be specifically a so-called metal thin film type magnetic recording medium in which a magnetic layer consisting of a metallic, magnetic thin film formed by, e.g., a vapor deposition process, a carbon film layer, and a lubricant layer including the partially-fluorinated-alkyl compound of the present invention are at least successively formed on a nonmagnetic support. If desired, an undercoat layer may be formed between the nonmagnetic support and the magnetic layer.

With respect to the nonmagnetic support, there is no particular limitation, and one which is conventionally known can be used. For example, when a substrate having stiffness, such as an Al alloy plate or a glass plate, used as a nonmagnetic support, an oxide film may be formed by an adonized aluminum treatment or a Ni—P film may be formed on the surface of the substrate so that the surface is hardened.

With respect to the metallic, magnetic thin film constituting the magnetic layer, there is no particular limitation, and one which is conventionally known can be used. Examples include metallic, magnetic thin films in the form of a continuous film formed by an electroplating, sputtering, or vacuum vapor deposition process, specifically include in-plane magnetized recording metallic, magnetic thin films consisting of a metal, such as Fe, Co, or Ni, a Co—Ni alloy, a Co—Pt alloy, a Co—Pt—Ni alloy, an Fe—Co alloy, an Fe—Ni alloy, an Fe—Co—Ni alloy, an Fe—Ni—B alloy, an Fe—Co—B alloy, or an Fe—Co—Ni—B alloy, and Co—Cr alloy magnetic thin films. Especially when an in-plane magnetized recording metallic, magnetic thin film is used, an undercoat layer consisting of a low melting-point nonmagnetic material, such as Bi, Sb, Pb, Sn, Ga, In, Ge, Si, or Tl, may be preliminarily formed on the nonmagnetic support, and the above metal may be deposited on the undercoat layer in the direction perpendicular to the undercoat layer by a vapor deposition or sputtering process to diffuse the low melting-point nonmagnetic material to the metallic, magnetic thin film so that the orientation of the metallic, magnetic thin film is cancelled to secure the in-plane isotropy and the coercive properties are improved.

As a method for forming the carbon film layer, a sputtering process is generally used, but there is no particular limitation and any known methods can be employed. The carbon film preferably has a thickness of 2 to 100 nm, further preferably 5 to 30 nm.

The lubricant layer can be formed by applying, as a topcoat, a lubricant including the partially-fluorinated-alkyl compound of the present invention onto the carbon film layer by a general method. The coating weight of the lubricant is preferably, for example, 0.5 to 100 mg/m$^2$, further preferably 1 to 20 mg/m$^2$. In formation of the lubricant layer by application, a solution obtained by dissolving a lubricant in an organic solvent, such as hexane, can be used. When a rust preventing agent is used, it may be used in the form of a mixture with a lubricant, but, when a rust preventing agent is first applied to the carbon film layer and then a lubricant is applied onto the rust preventing agent so that they constitute two or more different layers, the rust preventing effect is advantageously increased.

It is preferred that the partially-fluorinated-alkyl compound of the present invention is used as a lubricant for recording medium, especially for magnetic recording medium. However, the lubricant of the present invention can be applied not only to magnetic recording media but also to optical recording media. In addition, the support is not limited to a tape but can be used in recording media, such as disc media, e.g., magnetic discs and optical discs.

In conventional lubricants, a compound having a relatively high polarity, such as a carboxylic acid, an amine, or a carboxylic acid amine salt, has a small coefficient of friction, but it is poor in the still durability, and a compound having a relatively low polarity, such as an ester compound, has excellent still durability, but it has a large coefficient of friction. The partially-fluorinated-alkyl compound of the present invention has an aromatic ring or a heterocyclic group and two ester groups as terminal polar groups, and hence the compound has such excellent properties that the coefficient of friction is small and the still durability is excellent. Especially when the partially-fluorinated-alkyl compound of the present invention is applied as a lubricant to the carbon film layer, the aromatic ring or heterocyclic group and two ester groups in formula (1), which constitute the polar group portion of the lubricant molecule, adsorb onto the carbon film layer, thus making it possible to form a lubricant layer having more excellent durability due to the cohesion between the hydrophobic groups. Further, the application of a conventional fluorine-containing lubricant needs a fluorine solvent, but, in contrast, the partially-fluorinated-alkyl compound of the present invention advantageously enables application using a hydrocarbon solvent, such as toluene or acetone, thus lowering the load on the environment.

EXAMPLES OF THE FIRST EMBODIMENT

Hereinbelow, the present invention will be described in more detail with reference to the following Examples and Comparative Examples, which should not be construed as limiting the scope of the present invention.

Synthesis Example 1

Synthesis of $C_{18}H_{37}$—$CH(CH_2COOC_{10}H_6OH)COO(CH_2)_2(CF_2)_8F$

Using octadecylsuccinic anhydride as a succinic acid derivative having the substituent R in formula (1), a fluoroalcohol $\{F(CF_2)_8CH_2CH_2OH\}$ as an alcohol compound having the partially-fluorinated-alkyl group (Rf) in formula (1), and 2,3-naphthalenediol $\{C_{10}H_6(OH)_2\}$ as a hydroxyl compound having the substituent X in formula (1), a partially-fluorinated-alkyl compound of the present invention was synthesized. The procedure for the synthesis is shown below.

17.7 g of octadecylsuccinic anhydride ($C_{18}H_{37}C_4H_3O_3$) and 23.2 g of fluoroalcohol $\{F(CF_2)_8CH_2CH_2OH\}$ were mixed together and heated under reflux at 120° C. to effect a reaction for 3 hours. After completion of the reaction, the resultant reaction mixture was dissolved in 200 ml of toluene, and 300 ml of a 10% aqueous NaOH solution was added to the resultant solution and vigorously shaken. The resultant white solid matter (Na salt which is a desired product) was taken out by suction filtration using a glass filter. Then, the white solid matter on the glass filter was washed with 240 ml of water twice and then with 200 ml of toluene once. By this operation, the octadecylsuccinic anhydride remaining unreacted could be removed from the white solid matter. Then, the resultant white solid matter was placed in a separatory funnel, and 300 ml of toluene and 300 ml of 7.2% HCl were added to the separatory funnel to wash the solid matter for desalination. Further, the solid matter was washed with 300 ml of 7.2% HCl twice and then with an aqueous solution of sodium chloride twice, and the toluene phase was recovered and dried using magnesium sulfate. After one hour, the magnesium sulfate was removed by filtration and the toluene phase was concentrated. Then, the recovered substance was purified by column chromatography. Conditions for the column are as follows: column packing material: silica gel; column temperature: room temperature; and eluent: mixed solvent including 30% of ethyl acetate and 70% of toluene.

The desired product is eluted through the column when using a mixed solvent including 30% of ethyl acetate and 70% of toluene as an eluent.

An IR analysis shows that the product recovered has a formula of $C_{18}H_{37}$—$CH(CH_2COOH)COO(CH_2)_2(CF_2)_8F$.

5.0 g of thionyl chloride was added to 33 g of purified $C_{18}H_{37}$—$CH(CH_2COOH)COO(CH_2)_2(CF_2)_8F$ and heated under reflux at 50° C. to effect a reaction for 2 hours. After completion of the reaction, the resultant reaction mixture was concentrated to recover a desired product.

An IR analysis shows that the product recovered has a formula of $C_{18}H_{37}$—$CH(CH_2COCl)COO(CH_2)_2(CF_2)_8F$.

Next, 6.5 g of 2,3-naphthalenediol $\{C_{10}H_6(OH)_2\}$ was added to purified $C_{18}H_{37}$—$CH(CH_2COCl)COO(CH_2)_2(CF_2)_8F$ and heated under reflux at 100° C. to effect a reaction for 2 hours. After completion of the reaction, the resultant reaction mixture was dissolved in 200 ml of toluene, and placed in a separatory funnel and washed with 300 ml of a 10% aqueous NaOH solution twice and then with an aqueous solution of sodium chloride twice, and the toluene phase was recovered and dried using magnesium sulfate. After one hour, the magnesium sulfate was removed by filtration, and the toluene phase was concentrated. Then, the substance recovered was purified by column chromatography. Conditions for the column are as follows: column packing material: silica gel; column temperature: room temperature; and eluent: toluene. The desired product is eluted through the column when using toluene as an eluent. The weight of the product recovered was 34 g, and the recovery rate was about 70%.

An IR analysis shows that the product recovered has a formula of (synthesis of

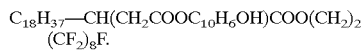

$C_{18}H_{37}$—$CH(CH_2COOC_{10}H_6OH)COO(CH_2)_2(CF_2)_8F$.

Synthesis Example 2

Synthesis of $C_{18}H_{37}$—$CH(CH_2COOC_{10}H_7)COO(CH_2)_2(CF_2)_8F$

An acid chloride having a formula of $C_{18}H_{37}$—$CH(CH_2COCl)COO(CH_2)_2(CF_2)_8F$ was synthesized in the same manner as in Synthesis Example 1.

Next, 5.9 g of 1-naphthol ($C_{10}H_7OH$) was added to purified $C_{18}H_{37}$—$CH(CH_2COCl)COO(CH_2)_2(CF_2)_8F$ and heated under reflux at 100° C. to effect a reaction for 2 hours. After completion of the reaction, the resultant reaction mixture was dissolved in 200 ml of toluene, and placed in a separatory funnel and washed with 300 ml of a 10% aqueous NaOH solution twice and then with an aqueous solution of sodium chloride twice, and the toluene phase was recovered and dried using magnesium sulfate. After one hour, the magnesium sulfate was removed by filtration and the toluene phase was concentrated. Then, the substance recovered was purified by column chromatography. Conditions for the column are as follows: column packing material: silica gel; column temperature: room temperature; and eluent: toluene. The desired product is eluted through the column when using toluene as an eluent. The weight of the product recovered was 34 g, and the recovery rate was about 70%.

An IR analysis shows that the product recovered has a formula of $C_{18}H_{37}$—$CH(CH_2COOC_{10}H_7)COO(CH_2)_2(CF_2)_8F$.

By employing the above-described procedure, the substituent R, partially-fluorinated-alkyl group (Rf), and substituent X in formula (1) can be arbitrarily selected to synthesize a partially-fluorinated-alkyl compound of the present invention. Specific examples of the partially-fluorinated-alkyl compounds synthesized are shown in Table 1 below.

TABLE 1

| Succinic acid derivative | Compound having Rf | Compound having X | Weight | Yield | Desired product |
|---|---|---|---|---|---|
| C8H17C4H3O3 10.5 g | F(CF2)8CH2CH2OH 23.2 g | 1-Naphthol 5.9 g | 28 g | 70% | C8H17—CH(CH2COOC10H7)COO(CH2)2(CF2)8F |
| C12H25C4H3O3 13.5 g | F(CF2)8CH2CH2OH 23.2 g | 1-Naphthol 5.9 g | 31 g | 70% | C12H25—CH(CH2COOC10H7)COO(CH2)2(CF2)8F |
| C18H35C4H3O3 17.5 g | F(CF2)8CH2CH2OH 23.2 g | 1-Naphthol 5.9 g | 34 g | 70% | C18H35—CH(CH2COOC10H7)COO(CH2)2(CF2)8F |
| C18H37C4H3O3 17.7 g | F(CF2)8CH2CH2OH 23.2 g | 2,3-Naphthalenediol 6.5 g | 34 g | 70% | C18H37—CH(CH2COOC10H6OH)COO(CH2)2(CF2)8F |
| C18H37C4H3O3 17.7 g | F(CF2)8(CH2)6OH 26.0 g | 2,3-Naphthalenediol 6.5 g | 35 g | 70% | C18H37—CH(CH2COOC10H6OH)COO(CH2)6(CF2)8F |
| C18H37C4H3O3 17.7 g | F(CF2)8(CH2)11OH 29.5 g | 2,3-Naphthalenediol 6.5 g | 31 g | 60% | C18H37—CH(CH2COOC10H6OH)COO(CH2)11(CF2)8F |
| C18H37C4H3O3 17.7 g | C18H37OH 13.5 g | 2,3-Naphthalenediol 6.5 g | 29 g | 75% | C18H37—CH(CH2COOC10H6OH)COOC18H37 |
| C18H37C4H3O3 17.7 g | C18H35OH 13.4 g | 2,3-Naphthalenediol 6.5 g | 29 g | 75% | C18H37—CH(CH2COOC10H6OH)COOC18H35 |
| C18H37C4H3O3 17.7 g | F(CF2)8CH2CH2OH 23.2 g | Phenol 4.3 g | 32 g | 70% | C18H37—CH(CH2COOC6H5)COOCH2CH2(CF2)8 |
| C18H37C4H3O3 17.7 g | F(CF2)8CH2CH2OH 23.2 g | 9-Anthracenemethanol 6.5 g | 30 g | 60% | C18H37—CH(CH2COOCH2C14H29)COOCH2CH2(CF2)8 |
| C18H37C4H3O3 17.7 g | F(CF2)8CH2CH2OH 23.2 g | 4-Hydroxypyridine 5.0 g | 26 g | 55% | C18H37—CH(CH2COOC5H4N)COOCH2CH2(CF2)8 |
| C18H37C4H3O3 17.7 g | F(CF2)8CH2CH2OH 23.2 g | o-Cresol 5.0 g | 25 g | 50% | C18H37—CH(CH2COOC6H4CH3)COOCH2CH2(CF2)8 |
| C18H37C4H3O3 17.7 g | F(CF2)8CH2CH2OH 23.2 g | 4-Aminophenol 6.0 g | 25 g | 50% | C18H37—CH(CH2COOC6H4NH)COOCH2CH2(CF2)8 |

TABLE 1-continued

| Succinic acid derivative | Compound having Rf | Compound having X | Weight | Yield | Desired product |
|---|---|---|---|---|---|
| C18H37C4H3O3 17.7 g | F(CF2)8CH2CH2OH 23.2 g | 4-Fluorophenol 6.0 g | 25 g | 50% | C18H37—CH(CH2COOC6H4F)COOCH2CH2(CF2)8 |
| C18H37C4H3O3 17.7 g | F(CF2)8CH2CH2OH 23.2 g | 4-Hydroxybenzoic acid 5.5 g | 25 g | 50% | C18H37—CH(CH2COOC6H4COOH)COOCH2CH2(CF2)8 |
| C18H37C4H3O3 17.7 g | F(CF2)8CH2CH2OH 23.2 g | 4-Phenylphenol 6.0 g | 33 g | 70% | C18H37—CH(CH2COOC6H4C6H5)COOCH2CH2(CF2)8 |

Examples 1 to 27

Partially-fluorinated-alkyl compounds of the present invention having the structures shown in Table 2 below were individually synthesized in accordance with the same procedure as in the above Synthesis Examples, and, with respect to each of the compounds synthesized, the tests shown below in respect of lubricant were conducted.

TABLE 2

| Example | Succinic acid derivative | Compound having Rf | Compound having X |
|---|---|---|---|
| 1 | $C_8H_{17}C_4H_3O_3$ | $F(CF_2)_8CH_2CH_2OH$ | 1-Naphthol |
| 2 | $C_{10}H_{21}C_4H_3O_3$ | $F(CF_2)_8CH_2CH_2OH$ | 1-Naphthol |
| 3 | $C_{12}H_{25}C_4H_3O_3$ | $F(CF_2)_8CH_2CH_2OH$ | 1-Naphthol |
| 4 | $C_{14}H_{29}C_4H_3O_3$ | $F(CF_2)_8CH_2CH_2OH$ | 1-Naphthol |
| 5 | $C_{16}H_{33}C_4H_3O_3$ | $F(CF_2)_8CH_2CH_2OH$ | 1-Naphthol |
| 6 | $C_{18}H_{37}C_4H_3O_3$ | $F(CF_2)_8CH_2CH_2OH$ | 1-Naphthol |
| 7 | $C_{18}H_{35}C_4H_3O_3$ | $F(CF_2)_8CH_2CH_2OH$ | 1-Naphthol |
| 8 | $C_{18}H_{37}C_4H_3O_3$ | $F(CF_2)_8(CH_2)_6OH$ | 2,3-Naphthalenediol |
| 9 | $C_{18}H_{37}C_4H_3O_3$ | $F(CF_2)_8(CH_2)_{11}OH$ | 2,3-Naphthalenediol |
| 10 | $C_{18}H_{37}C_4H_3O_3$ | $C_{18}H_{37}OH$ | 2,3-Naphthalenediol |
| 11 | $C_{18}H_{37}C_4H_3O_3$ | $C_{18}H_{35}OH$ | 2,3-Naphthalenediol |
| 12 | $C_8H_{17}C_4H_3O_3$ | $F(CF_2)_8CH_2CH_2OH$ | 2,3-Naphthalenediol |
| 13 | $C_{10}H_{21}C_4H_3O_3$ | $F(CF_2)_8CH_2CH_2OH$ | 2,3-Naphthalenediol |
| 14 | $C_{12}H_{25}C_4H_3O_3$ | $F(CF_2)_8CH_2CH_2OH$ | 2,3-Naphthalenediol |
| 15 | $C_{14}H_{29}C_4H_3O_3$ | $F(CF_2)_8CH_2CH_2OH$ | 2,3-Naphthalenediol |
| 16 | $C_{18}H_{33}C_4H_3O_3$ | $F(CF_2)_8CH_2CH_2OH$ | 2,3-Naphthalenediol |
| 17 | $C_{18}H_{37}C_4H_3O_3$ | $F(CF_2)_8CH_2CH_2OH$ | 2,3-Naphthalenediol |
| 18 | $C_9H_{19}CH(C_7H_{15})C_4H_3O_3$ | $F(CF_2)_8CH_2CH_2OH$ | 2,3-Naphthalenediol |
| 19 | $C_{18}H_{35}C_4H_3O_3$ | $F(CF_2)_8CH_2CH_2OH$ | 2,3-Naphthalenediol |
| 20 | $C_{18}H_{37}C_4H_3O_3$ | $F(CF_2)_8CH_2CH_2OH$ | Phenol |
| 21 | $C_{18}H_{37}C_4H_3O_3$ | $F(CF_2)_8CH_2CH_2OH$ | 9-Anthracenemethanol |
| 22 | $C_{18}H_{37}C_4H_3O_3$ | $F(CF_2)_8CH_2CH_2OH$ | 4-Hydroxypyridine |
| 23 | $C_{18}H_{37}C_4H_3O_3$ | $F(CF_2)_8CH_2CH_2OH$ | o-Cresol |
| 24 | $C_{18}H_{37}C_4H_3O_3$ | $F(CF_2)_8CH_2CH_2OH$ | 4-Aminophenol |
| 25 | $C_{18}H_{37}C_4H_3O_3$ | $F(CF_2)_8CH_2CH_2OH$ | 4-Fluorophenol |
| 26 | $C_{18}H_{37}C_4H_3O_3$ | $F(CF_2)_8CH_2CH_2OH$ | 4-Hydroxybenzoic acid |
| 27 | $C_{18}H_{37}C_4H_3O_3$ | $F(CF_2)_8CH_2CH_2OH$ | 4-Phenylphenol |

Comparative Examples 1 to 5

With respect to each of the compounds having the structures in Table 3 below, the tests shown below in respect of ant were conducted.

TABLE 3

| Comp. Exp. | Compound |
|---|---|
| 1 | $C_{18}H_{37}NH_2$ |
| 2 | $C_8F_{17}(CF_2)_{10}COOCH_3$ |
| 3 | $C_{18}H_{37}CH(COOC_{12}H_{25})C_2H_4COOCH_2CF_2(OCF_2)_p$ $[OCF(CF_3)CF_2]_qOCF_3$ (average molecular weight: 2,140) |
| 4 | $C_{18}H_{37}CH(COOH)CH_2COOCH_2CF(CF_3)[CF(CF_3)CF_2O]_3F$ |
| 5 | $C_{11}H_{23}COORfOCOC_{11}H_{23}$ |

TABLE 3-continued

| Comp. Exp. | Compound |
|---|---|

(Rf represents a perfluoropolyether chain having an average molecular weight of 2,000)

Preparation of Sample Tape

Co was deposited on a polyethylene terephthalate film having a thickness of 7.0 µm by a vapor deposition process to form a magnetic layer having a thickness of 180 nm consisting of a metallic, magnetic thin film. Then, a carbon film, layer having a thickness of about 8 nm was formed on the magnetic layer using a magnetron sputtering apparatus.

Next, on another surface of the polyethylene terephthalate film that is not the surface on which the magnetic layer was formed, a back coat layer having a thickness of 0.5 μm consisting of carbon and a polyurethane resin was formed.

Then, the compounds shown in Tables 2 and 3 were individually dissolved in toluene, and the resultant solutions were individually applied to the surface of the carbon film layer previously formed so that the coating weight of each compound became 5 mg/m². The magnetic recording media obtained were individually cut into 6.35 mm-width tapes to obtain sample tapes.

Evaluation of Durability and Transport Properties

With respect to each of the thus prepared sample tapes, a coefficient of friction, still durability, and shuttle durability were measured under, respectively, conditions at a temperature of 40° C. at a relative humidity of 80%, conditions at a temperature of 5° C., and conditions at a temperature of 40° C. at a relative humidity of 20%. The results are shown in Table 4.

It is considered that the conditions for measurements used in the Examples are most severe conditions for use with respect to each tape. In the measurements of the still durability and shuttle durability, a commercially available digital video camcorder (manufactured and sold by Sony Corporation; trade name: VX1000) was used.

(1) Method for Measurement of Coefficient of Friction

The coefficient of friction was measured as follows. In a thermostatic chamber controlled at a temperature of 40° C. at a relative humidity of 80%, each sample tape was subjected to 100-cycle transport by means of an apparatus for measuring a coefficient of friction. The measurement values after the 100th-cycle transport are shown as coefficient of friction in the Table below.

(2) Method for Measurement of Still Durability

The still durability was measured as follows. In a thermostatic chamber at 5° C., a period of time until the replay output was lowered by 3 dB was measured.

(3) Method for Measurement of Shuttle Durability

The shuttle durability was measured as follows In a thermostatic chamber controlled at a temperature of 40° C. at a relative humidity of 20%, each sample tape having a length corresponding to 60 minutes was subjected to 100-cycle transport in a Play mode, and a value (dB) was determined by subtracting the replay output after the 100th-cycle transport from the initial output.

Evaluation of Solubility in Solvent

With respect to each of the lubricants used in Examples 1 to 27 and Comparative Example 3, the solubility in solvents, i.e., ethanol, acetone, and toluene was examined. The solubility was evaluated in accordance with the following criteria: a lubricant easily dissolved in the solvent was rated symbol ○; and a lubricant insoluble in the solvent was rated symbol ×. The results of the evaluation of solubility of the lubricants are shown in Table 5 below.

As is apparent from the above results, when the partially-fluorinated-alkyl compound of the first embodiment is used as a lubricant for magnetic recording medium, very excellent results are obtained such that the coefficient of friction and deterioration of the still durability and shuttle durability are extremely small under various conditions for use, e.g., at a high temperature at a high humidity, at a high temperature at a low humidity, or at a low temperature.

Second Embodiment

A partially-fluorinated-alkyl compound according to a second embodiment of the present invention may be synthesized, for example, as follows.

First, a succinic acid derivative having the substituent R in formula (2) and an alcohol compound having the fluoroalkyl group (Rf) in formula (2) are mixed together and heated to 150° C. to effect a reaction, and then, impurities and the remaining unnecessary substances are removed from the resultant reaction mixture by washing with an organic solvent or an inorganic solvent, extraction using a separatory funnel, or purification by column chromatography to obtain a partially-fluorinated-alkyl monoester monocarboxylic acid compound purified. Then, the obtained partially-fluorinated-alkyl monoester monocarboxylic acid compound and a hydroxyl compound having the substituent X in formula (2) are subjected to esterification so that one hydroxyl group in the hydroxyl compound having the substituent X is reacted with one carboxyl group in the partially-fluorinated-alkyl monoester monocarboxylic acid compound to form an ester linkage, followed by purification, thus obtaining a partially-fluorinated-alkyl compound.

In the esterification, a method can be employed in which the carboxyl group in the partially-fluorinated-alkyl monoester monocarboxylic acid compound is preliminarily treated with, e.g., thionyl chloride to form an acid chloride, and then reacted with the hydroxyl group in the hydroxyl compound having the substituent X.

As mentioned above, the partially-fluorinated-alkyl compound of the present invention can be advantageously used as a lubricant for recording medium, especially for magnetic recording medium. If desired, various additives, for example, a rust preventing agent can be added to the lubricant. As a rust preventing agent, one which has conventionally been used for magnetic recording medium can be used, and examples include phenols, naphthols, quinones, heterocyclic compounds containing a nitrogen atom, heterocyclic compounds containing an oxygen atom, and heterocyclic compounds containing a sulfur atom.

The recording medium of the present invention includes a lubricant layer including the above lubricant. For example, when the recording medium of the present invention is a magnetic recording medium, it can be specifically a so-called metal thin film type magnetic recording medium in which a magnetic layer consisting of a metallic, magnetic thin film formed by, e.g., a vapor deposition process, a carbon film layer, and a lubricant layer including the partially-fluorinated-alkyl compound of the present invention are at least successively formed on a nonmagnetic support. If desired, an undercoat layer may be formed between the nonmagnetic support and the magnetic layer.

With respect to the nonmagnetic support, there is no particular limitation, and one which is conventionally known can be used. For example, when a substrate having stiffness, such as an Al alloy plate or a glass plate, used as a nonmagnetic support, an oxide film may be formed by an adonized aluminum treatment or a Ni—P film may be formed on the surface of the substrate so that the surface is hardened.

With respect to the metallic, magnetic thin film constituting the magnetic layer, there is no particular limitation, and one which is conventionally known can be used. Examples include metallic, magnetic thin films in the form of a continuous film formed by an electroplating, sputtering, or vacuum vapor deposition process, specifically include in-plane magnetized recording metallic, magnetic thin films consisting of a metal, such as Fe, Co, or Ni, a Co—Ni alloy, a Co—Pt alloy, a Co—Pt—Ni alloy, an Fe—Co alloy, an Fe—Ni alloy, an Fe—Co—Ni alloy, an Fe—Ni—B alloy, an Fe—Co—B alloy, or an Fe—Co—Ni—B alloy, and Co—Cr alloy magnetic thin films. Especially when an in-plane magnetized recording metallic, magnetic thin film is used, an undercoat layer consisting of a low melting-point nonmagnetic material, such as Bi, Sb, Pb, Sn, Ga, In, Ge, Si, or Tl, may be preliminarily formed on the nonmagnetic support, and the above metal may be deposited on the undercoat layer in the direction perpendicular to the undercoat layer by a vapor deposition or sputtering process to diffuse the low melting-point nonmagnetic material to the metallic, magnetic thin film so that the orientation of the metallic, magnetic thin film is cancelled to secure the in-plane isotropy and the coercive properties are improved.

As a method for forming the carbon film layer, a sputtering process is generally used, but there is no particular limitation and any known methods can be employed. The carbon film preferably has a thickness of 2 to 100 nm, further preferably 5 to 30 nm.

The lubricant layer can be formed by applying, as a topcoat, a lubricant including the partially-fluorinated-alkyl compound of the present invention onto the carbon film layer by a general method. The coating weight of the lubricant is preferably, for example, 0.5 to 100 mg/m$^2$, further preferably 1 to 20 mg/m$^2$. In formation of the lubricant layer by application, a solution obtained by dissolving a lubricant in an organic solvent, such as hexane, can be used. When a rust preventing agent is used, it may be used in the form of a mixture with a lubricant, but, when a rust preventing agent is first applied to the carbon film layer and then a lubricant is applied onto the rust preventing agent so that they constitute two or more different layers, the rust preventing effect is advantageously increased.

It is preferred that the partially-fluorinated-alkyl compound of the present invention is used as a lubricant for recording medium, especially for magnetic recording medium. However, the lubricant of the present invention can be applied not only to magnetic recording media but also to optical recording media. In addition, the support is not limited to a tape but can be used in recording media, such as disc media, e.g., magnetic discs and optical discs.

In conventional lubricants, a compound having a relatively high polarity, such as a carboxylic acid, an amine, or a carboxylic acid amine salt, has a small coefficient of friction, but it is poor in the still durability, and a compound having a relatively low polarity, such as an ester compound, has excellent still durability, but it has a large coefficient of friction. The partially-fluorinated-alkyl compound of the present invention has an aromatic ring or a heterocyclic group and two ester groups as terminal polar groups, and hence the compound has such excellent properties that the coefficient of friction is small and the still durability is excellent. Especially when the partially-fluorinated-alkyl compound of the present invention is applied as a lubricant to the carbon film layer, the aromatic ring or heterocyclic group and two ester groups in formula (2), which constitute the polar group portion of the lubricant molecule, adsorb onto the carbon film layer, thus making it possible to form a lubricant layer having more excellent durability due to the cohesion between the hydrophobic groups. Further, the application of a conventional fluorine-containing lubricant needs a fluorine solvent, but, in contrast, the partially-fluorinated-alkyl compound of the present invention advantageously enables application using a hydrocarbon solvent, such as toluene or acetone, thus lowering the load on the environment.

EXAMPLES OF THE SECOND EMBODIMENT

Hereinbelow, the present invention will be described in more detail with reference to the following Examples and Comparative Examples, which should not be construed as limiting the scope of the present invention.

Synthesis Example 1

Synthesis of $C_{18}H_{37}$—CH(CH$_2$COO(CH$_2$)$_2$(CF$_2$)$_8$F)COOC$_{10}$H$_6$OH Using octadecylsuccinic anhydride as a succinic acid derivative having the substituent R in formula (2), a fluoroalcohol {F(CF$_2$)$_8$CH$_2$CH$_2$OH} as an alcohol compound having the partially-fluorinated-alkyl group (Rf) in formula (2), and 2,3-naphthalenediol {C$_{10}$H$_6$(OH)$_2$} as a hydroxyl compound having the substituent X in formula (2), a partially-fluorinated-alkyl compound of the present invention was synthesized. The procedure for the synthesis is shown below.

17.7 g of octadecylsuccinic anhydride (C$_{18}$H$_{37}$C$_4$H$_3$O$_3$) and 23.2 g of fluoroalcohol {F(CF$_2$)$_8$CH$_2$CH$_2$OH} were mixed together and heated under reflux at 120° C. to effect a reaction for 3 hours. After completion of the reaction, the resultant reaction mixture was dissolved in 200 ml of toluene, and 300 ml of a 10% aqueous NaOH solution was added to the resultant solution and vigorously shaken. The resultant white solid matter (Na salt which is a desired product) was taken out by suction filtration using a glass filter. Then, the white solid matter on the glass filter was washed with 240 ml of water twice and then with 200 ml of toluene once. By this operation, the octadecylsuccinic anhydride remaining unreacted could be removed from the white solid matter. Then, the resultant white solid matter was placed in a separatory funnel, and 300 ml of toluene and 300 ml of 7.2% HCl were added to the separatory funnel to wash the solid matter for desalination. Further, the solid matter was washed with 300 ml of 7.2% HCl twice and then with an aqueous solution of sodium chloride twice, and the toluene phase was recovered and dried using magnesium sulfate. After one hour, the magnesium sulfate was removed by filtration and the toluene phase was concentrated. Then, the recovered substance was purified by column chromatography. Conditions for the column are as follows: column packing material: silica gel; column temperature: room temperature; and eluent: mixed solvent including 30% of ethyl acetate and 70% of toluene.

The desired product is eluted through the column when using a mixed solvent including 30% of ethyl acetate and 70% of toluene as an eluent.

An IR analysis shows that the product recovered has a formula of $C_{18}H_{37}$—CH(CH$_2$COO(CH$_2$)$_2$(CF$_2$)$_8$F)COOH.

5.0 g of thionyl chloride was added to 33 g of purified $C_{18}H_{37}$—CH(CH$_2$COO(CH$_2$)$_2$(CF$_2$)$_8$F)COOH and heated under reflux at 50° C. to effect a reaction for 2 hours. After completion of the reaction, the resultant reaction mixture was concentrated to recover a desired product.

An IR analysis shows that the product recovered has a formula of $C_{18}H_{37}$—CH(CH$_2$COO(CH$_2$)$_2$(CF$_2$)$_8$F)COCl.

Next, 6.5 g of 2,3-naphthalenediol {C$_{10}$H$_6$(OH)$_2$} was added to purified $C_{18}H_{37}$—CH(CH$_2$COO(CH$_2$)$_2$(CF$_2$)$_8$F)COCl and heated under reflux at 100° C. to effect a reaction for 2 hours. After completion of the reaction, the resultant reaction mixture was dissolved in 200 ml of toluene, and placed in a separatory funnel and washed with 300 ml of a 10% aqueous NaOH solution twice and then with an aqueous solution of sodium chloride twice, and the toluene phase was recovered and dried using magnesium sulfate. After one hour, the magnesium sulfate was removed by filtration, and the toluene phase was concentrated. Then, the substance recovered was purified by column chromatography. Conditions for the column are as follows: column packing material: silica gel; column temperature: room temperature; and eluent: toluene. The desired product is eluted through the column when using toluene as an eluent. The weight of the product recovered was 34 g, and the recovery rate was about 70%.

An IR analysis shows that the product recovered has a formula of $C_{18}H_{37}$—$CH(CH_2COO(CH_2)_2(CF_2)_8F)COOC_{10}H_6OH$.

Synthesis Example 2

Synthesis of $C_{18}H_{37}$—$CH(CH_2COO(CH_2)_2(CF_2)_8F)COOC_{10}H_7$

An acid chloride having a formula of $C_{18}H_{37}$—$CH(CH_2COO(CH_2)_2(CF_2)_8F)COCl$ was synthesized in the same manner as in Synthesis Example 1.

Next, 5.9 g of 1-naphthol ($C_{10}H_7OH$) was added to purified $C_{18}H_{37}$—$CH(CH_2COO(CH_2)_2(CF_2))COCl_8$ and heated under reflux at 100° C. to effect a reaction for 2 hours. After completion of the reaction, the resultant reaction mixture was dissolved in 200 ml of toluene, and placed in a separatory funnel and washed with 300 ml of a 10% aqueous NaOH solution twice and then with an aqueous solution of sodium chloride twice, and the toluene phase was recovered and dried using magnesium sulfate. After one hour, the magnesium sulfate was removed by filtration and the toluene phase was concentrated. Then, the substance recovered was purified by column chromatography. Conditions for the column are as follows: column packing material: silica gel; column temperature: room temperature; and eluent: toluene. The desired product is eluted through the column when using toluene as an eluent. The weight of the product recovered was 34 g, and the recovery rate was about 70%.

An IR analysis shows that the product recovered has a formula of $C_{18}H_{37}$—$CH(CH_2COO(CH_2)_2(CF_2)_8F)COOC_{10}H_7$.

By employing the above-described procedure, the substituent R, partially-fluorinated-alkyl group (Rf), and substituent X in formula (2) can be arbitrarily selected to synthesize a partially-fluorinated-alkyl compound of the present invention. Specific examples of the partially-fluorinated-alkyl compounds synthesized are shown in Table 6 below.

TABLE 6

| Succinic acid derivative | Compound having Rf | Compound having X | Weight | Yield | Desired product |
|---|---|---|---|---|---|
| C8H17C4H3O3 10.5 g | F(CF2)8CH2CH2OH 23.2 g | 1-Naphthol 5.9 g | 28 g | 70% | C8H17—CH(CH2COO(CH2)2(CF2)8F)7COOC10H7 |
| C12H25C4H3O3 13.5 g | F(CF2)8CH2CH2OH 23.2 g | 1-Naphthol 5.9 g | 31 g | 70% | C12H25—CH(CH2COO(CH2)2(CF2)8F)7COO C10H7 |
| C18H35C4H3O3 17.5 g | F(CF2)8CH2CH2OH 23.2 g | 1-Naphthol 5.9 g | 34 g | 70% | C18H35—CH(CH2COO(CH2)2(CF2)8F)7COOC10H7 |
| C18H37C4H3O3 17.7 g | F(CF2)8CH2CH2OH 23.2 g | 2,3-Naphthalenediol 6.5 g | 34 g | 70% | C18H37—CH(CH2COO(CH2)2(CF2)8F)COOC10H6 OH |
| C18H37C4H3O3 17.7 g | F(CF2)8(CH2)6OH 26.0 g | 2,3-Naphthalenediol 6.5 g | 35 g | 70% | C18H37—CH(CH2COO(CH2)2(CF2)8F)COO C10H6OH |
| C18H37C4H3O3 17.7 g | F(CF2)8(CH2)11OH 29.5 g | 2,3-Naphthalenediol 6.5 g | 31 g | 60% | C18H37—CH(CH2COO(CH2)2(CF2)8F)COO C10H6OH |
| C18H37C4H3O3 17.7 g | C18H37OH 13.5 g | 2,3-Naphthalenediol 6.5 g | 29 g | 75% | C18H37—CH(CH2COOC18 H37)COO C10H6OH |
| C18H37C4H3O3 17.7 g | C18H35OH 13.4 g | 2,3-Naphthalenediol 6.5 g | 29 g | 75% | C18H37—CH(CH2COOC18 H37)COO C10H6OH |
| C18H37C4H3O3 17.7 g | F(CF2)8CH2CH2OH 23.2 g | Phenol 4.3 g | 32 g | 70% | C18H37—CH(CH2COOCH2 CH2(CF2)8)COO C6H5 |
| C18H37C4H3O3 17.7 g | F(CF2)8CH2CH2OH 23.2 g | 9-Anthracenemethanol 6.5 g | 30 g | 60% | C18H37—CH(CH2COOCH2 CH2(CF2)8) COO CH2C14H9 |
| C18H37C4H3O3 17.7 g | F(CF2)8CH2CH2OH 23.2 g | 4-Hydroxypyridine 5.0 g | 26 g | 55% | C18H37—CH(CH2COOCH2 CH2(CF2)8) COO C5H4N |
| C18H37C4H3O3 17.7 g | F(CF2)8CH2CH2OH 23.2 g | o-Cresol 5.0 g | 25 g | 50% | C18H37—CH(CH2COOCH2 CH2(CF2)8) COOC6H4CH3 |
| C18H37C4H3O3 17.7 g | F(CF2)8CH2CH2OH 23.2 g | 4-Aminophenol 6.0 g | 25 g | 50% | C18H37—CH(CH2COOCH2 CH2(CF2)8) COO C6H4NH |
| C18H37C4H3O3 17.7 g | F(CF2)8CH2CH2OH 23.2 g | 4-Fluorophenol 6.0 g | 25 g | 50% | C18H37—CH(CH2COOCH2 CH2(CF2)8) COO C6H4F |
| C18H37C4H3O3 17.7 g | F(CF2)8CH2CH2OH 23.2 g | 4-Hydroxybenzoic acid 5.5 g | 25 g | 50% | C18H37—CH(CH2COOCH2 CH2(CF2)8) COO C6H4COOH |
| C18H37C4H3O3 17.7 g | F(CF2)8CH2CH2OH 23.2 g | 4-Phenylphenol 6.0 g | 33 g | 70% | C18H37—CH(CH2COOCH2 CH2(CF2)8) COO C6H4C6H5 |

Examples 1 to 2–7

Partially-fluorinated-alkyl compounds of the present invention having the structures shown in Table 7 below were individually synthesized in accordance with the same procedure as in the above Synthesis Examples, and, with respect to each of the compounds synthesized, the tests shown below in respect of lubricant were conducted.

TABLE 7

| Example | Succinic acid derivative | Compound having Rf | Compound having X |
|---|---|---|---|
| 1 | $C_8H_{17}C_4H_3O_3$ | $F(CF_2)_8CH_2CH_2OH$ | 1-Naphthol |
| 2 | $C_{10}H_{21}C_4H_3O_3$ | $F(CF_2)_8CH_2CH_2OH$ | 1-Naphthol |
| 3 | $C_{12}H_{25}C_4H_3O_3$ | $F(CF_2)_8CH_2CH_2OH$ | 1-Naphthol |
| 4 | $C_{14}H_{29}C_4H_3O_3$ | $F(CF_2)_8CH_2CH_2OH$ | 1-Naphthol |
| 5 | $C_{16}H_{33}C_4H_3O_3$ | $F(CF_2)_8CH_2CH_2OH$ | 1-Naphthol |
| 6 | $C_{18}H_{37}C_4H_3O_3$ | $F(CF_2)_8CH_2CH_2OH$ | 1-Naphthol |
| 7 | $C_{18}H_{35}C_4H_3O_3$ | $F(CF_2)_8CH_2CH_2OH$ | 1-Naphthol |
| 8 | $C_{18}H_{37}C_4H_3O_3$ | $F(CF_2)_8(CH_2)_6OH$ | 2,3-Naphthalenediol |
| 9 | $C_{18}H_{37}C_4H_3O_3$ | $F(CF_2)_8(CH_2)_{11}OH$ | 2,3-Naphthalenediol |
| 10 | $C_{18}H_{37}C_4H_3O_3$ | $C_{18}H_{37}OH$ | 2,3-Naphthalenediol |
| 11 | $C_{18}H_{37}C_4H_3O_3$ | $C_{18}H_{35}OH$ | 2,3-Naphthalenediol |
| 12 | $C_{18}H_{17}C_4H_3O_3$ | $F(CF_2)_8CH_2CH_2OH$ | 2,3-Naphthalenediol |
| 13 | $C_{10}H_{21}C_4H_3O_3$ | $F(CF_2)_8CH_2CH_2OH$ | 2,3-Naphthalenediol |
| 14 | $C_{12}H_{25}C_4H_3O_3$ | $F(CF_2)_8CH_2CH_2OH$ | 2,3-Naphthalenediol |
| 15 | $C_{14}H_{29}C_4H_3O_3$ | $F(CF_2)_8CH_2CH_2OH$ | 2,3-Naphthalenediol |
| 16 | $C_{18}H_{33}C_4H_3O_3$ | $F(CF_2)_8CH_2CH_2OH$ | 2,3-Naphthalenediol |
| 17 | $C_{18}H_{37}C_4H_3O_3$ | $F(CF_2)_8CH_2CH_2OH$ | 2,3-Naphthalenediol |
| 18 | $C_9H_{19}CH(C_7H_{15})C_4H_3O_3$ | $F(CF_2)_8CH_2CH_2OH$ | 2,3-Naphthalenediol |
| 19 | $C_{18}H_{35}C_4H_3O_3$ | $F(CF_2)_8CH_2CH_2OH$ | 2,3-Naphthalenediol |
| 20 | $C_{18}H_{37}C_4H_3O_3$ | $F(CF_2)_8CH_2CH_2OH$ | Phenol |
| 21 | $C_{18}H_{37}C_4H_3O_3$ | $F(CF_2)_8CH_2CH_2OH$ | 9-Anthracenemethanol |
| 22 | $C_{18}H_{37}C_4H_3O_3$ | $F(CF_2)_8CH_2CH_2OH$ | 4-Hydroxypyridine |
| 23 | $C_{18}H_{37}C_4H_3O_3$ | $F(CF_2)_8CH_2CH_2OH$ | o-Cresol |
| 24 | $C_{18}H_{37}C_4H_3O_3$ | $F(CF_2)_8CH_2CH_2OH$ | 4-Aminophenol |
| 25 | $C_{18}H_{37}C_4H_3O_3$ | $F(CF_2)_8CH_2CH_2OH$ | 4-Fluorophenol |
| 26 | $C_{18}H_{37}C_4H_3O_3$ | $F(CF_2)_8CH_2CH_2OH$ | 4-Hydroxybenzoic acid |
| 27 | $C_{18}H_{37}C_4H_3O_3$ | $F(CF_2)_8CH_2CH_2OH$ | 4-Phenylphenol |

Comparative Examples 1 to 5

With respect to each of the compounds having the structures shown in Table 8 below, the tests shown below in respect of lubricant were conducted.

TABLE 8

| Comp. Exp. | Compound |
|---|---|
| 1 | $C_{18}H_{37}NH_2$ |
| 2 | $C_8F_{17}(CF_2)_{10}COOCH_3$ |
| 3 | $C_{18}H_{37}CH(COOC_{12}H_{25})C_2H_4COOCH_2CF_2(OCF_2)_p[OCF(CF_3)CF_2]_qOCF_3$ (average molecular weight: 2,140) |
| 4 | $C_{18}H_{37}CH(COOH)CH_2COOCH_2CF(CF_3)[CF(CF_3)CF_2O]_3F$ |
| 5 | $C_{11}H_{23}COORfOCOC_{11}H_{23}$ (Rf represents a perfluoropolyether chain having an average molecular weight of 2,000) |

Preparation of Sample Tape

Co was deposited on a polyethylene terephthalate film having a thickness of 7.0 μm by a vapor deposition process to form a magnetic layer having a thickness of 180 nm consisting of a metallic, magnetic thin film. Then, a carbon film layer having a thickness of about 8 nm was formed on the magnetic layer using a magnetron sputtering apparatus.

Next, on another surface of the polyethylene terephthalate film that is not the surface on which the magnetic layer was formed, a back coat layer having a thickness of 0.5 μm consisting of carbon and a polyurethane resin was formed.

Then, the compounds shown in Tables 7 and 8 were individually dissolved in toluene, and the resultant solutions were individually applied to the surface of the carbon film layer previously formed so that the coating weight of each compound became 5 mg/m². The magnetic recording media obtained were individually cut into 6.35 mm-width tapes to obtain sample tapes.

Evaluation of Durability and Transport Properties

With respect to each of the thus prepared sample tapes, a coefficient of friction, still durability, and shuttle durability were measured under, respectively, conditions at a temperature of 40° C. at a relative humidity of 80%, conditions at a temperature of −5° C., and conditions at a temperature of 40° C. at a relative humidity of 20%. The results are shown in Table 9.

It is considered that the conditions for measurements used in the Examples are most severe conditions for use with respect to each tape. In the measurements of the still durability and shuttle durability, a commercially available digital video camcorder (manufactured and sold by Sony Corporation; trade name: VX1000) was used.

(1) Method for Measurement of Coefficient of Friction

The coefficient of friction was measured as follows. In a thermostatic chamber controlled at a temperature of 40° C. at a relative humidity of 80%, each sample tape was subjected to 100-cycle transport by means of an apparatus for measuring a coefficient of friction. The measurement values after the 100th-cycle transport are shown as coefficient of friction in the Table below.

(2) Method for Measurement of Still Durability

The still durability was measured as follows. In a thermostatic chamber at −5° C., a period of time until the replay output was lowered by 3 dB was measured.

(3) Method for Measurement of Shuttle Durability

The shuttle durability was measured as follows. In a thermostatic chamber controlled at a temperature of 40° C. at a relative humidity of 20%, each sample tape having a length corresponding to 60 minutes was subjected to 100-cycle transport in a Play mode, and a value (dB) was determined by subtracting the replay output after the 100th-cycle transport from the initial output.

Evaluation of Solubility in Solvent

With respect to each of the lubricants used in Examples 1 to 27 and Comparative Example 3, the solubility in solvents, i.e., ethanol, acetone, and toluene was examined. The solubility was evaluated in accordance with the following criteria: a lubricant easily dissolved in the solvent was rated symbol ○; and a lubricant insoluble in the solvent was rated symbol ×. The results of the evaluation of solubility of the lubricants are shown in Table 10 below.

TABLE 9

|  | Coefficient of friction (40° C., 80% RH) | Still durability (min) (−5° C.) | Shuttle durability (dB) (40° C., 20% RH) |
|---|---|---|---|
| Exp. 1 | 0.25 | >120 | −2.0 |
| Exp. 2 | 0.25 | >120 | −1.9 |
| Exp. 3 | 0.25 | >120 | −2.0 |
| Exp. 4 | 0.23 | >120 | −1.8 |
| Exp. 5 | 0.21 | >120 | −1.7 |
| Exp. 6 | 0.21 | >120 | −1.7 |
| Exp. 7 | 0.21 | >120 | −1.5 |
| Exp. 8 | 0.21 | >120 | −1.5 |
| Exp. 9 | 0.21 | >120 | −1.5 |
| Exp. 10 | 0.21 | >120 | −2.1 |
| Exp. 11 | 0.21 | >120 | −2.2 |
| Exp. 12 | 0.25 | >120 | −2.0 |
| Exp. 13 | 0.25 | >120 | −1.9 |
| Exp. 14 | 0.23 | >120 | −1.8 |
| Exp. 15 | 0.20 | >120 | −1.7 |
| Exp. 16 | 0.20 | >120 | −1.6 |
| Exp. 17 | 0.20 | >120 | −1.5 |
| Exp. 18 | 0.20 | >120 | −2.2 |
| Exp. 19 | 0.20 | >120 | −2.0 |
| Exp. 20 | 0.20 | >120 | −1.8 |
| Exp. 21 | 0.20 | >120 | −1.8 |
| Exp. 22 | 0.20 | >120 | −1.8 |
| Exp. 23 | 0.20 | >120 | −1.9 |
| Exp. 24 | 0.20 | >120 | −1.8 |
| Exp. 25 | 0.22 | >120 | −1.6 |
| Exp. 26 | 0.22 | >120 | −1.6 |
| Exp. 27 | 0.20 | >120 | −1.7 |
| Comp. Exp. 1 | 0.20 | 3 | −6.0 |
| Comp. Exp. 2 | 0.35 | 50 | −5.0 |
| Comp. Exp. 3 | 0.32 | >120 | −5.0 |
| Comp. Exp. 4 | 0.25 | 10 | −2.3 |
| Comp. Exp. 5 | 0.45 | 100 | −2.5 |

TABLE 10

| Compound | Ethanol | Acetone | Toluene |
|---|---|---|---|
| Exps. 1 to 27 | ○ | ○ | ○ |
| Comp. Exp. 3 | × | × | × |

As is apparent from the above results, when the partially-fluorinated-alkyl compound of the present invention is used as a lubricant for magnetic recording medium, very excellent results are obtained such that the coefficient of friction and deterioration of the still durability and shuttle durability are extremely small under various conditions for use, e.g., at a high temperature at a high humidity, at a high temperature at a low humidity, or at a low temperature.

While the present invention has been particularly shown and described with reference to preferred embodiments according to the present invention, it will be understood by those skilled in the art that any combinations or sub-combinations of the embodiments and/or other changes in form and details can be made therein without departing from the scope of the invention.

What is claimed is:

1. A partially-fluorinated-alkyl compound being represented by the following formula (1) or (2):

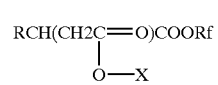

wherein R represents a saturated or unsaturated aliphatic hydrocarbon group having 6 to 30 carbon atoms; Rf represents a saturated or unsaturated fluoroalkyl group; and X represents an aromatic ring or a heterocyclic group, a hydrocarbon group substituted with an aromatic ring or heterocyclic group, or an aromatic ring or heterocyclic group substituted with: a hydroxyl group, an amino group, a carboxyl group, a halogen atom, a hydrocarbon group, or an aromatic ring.

2. A lubricant for recording medium, comprising a partially-fluorinated-alkyl compound represented by the following formula (1) or (2):

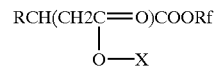

wherein R represents a saturated or unsaturated aliphatic hydrocarbon group having 6 to 30 carbon atoms; Rf represents a saturated or unsaturated fluoroalkyl group; and X represents an aromatic ring or a heterocyclic group, a hydrocarbon group substituted with an aromatic ring or heterocyclic group, or an aromatic ring or heterocyclic group substituted with: a hydroxyl group, an amino group, a carboxyl group, a halogen atom, a hydrocarbon group, or an aromatic ring.

3. A recording medium comprising a support, a recording layer, and a lubricant layer comprising a lubricant, wherein said recording layer and said lubricant layer are successively formed on said support,
wherein said lubricant includes a partially-fluorinated-alkyl compound represented by the following formula (1) or (2):

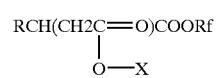

wherein R represents a saturated or unsaturated aliphatic hydrocarbon group having 6 to 30 carbon atoms; Rf represents a saturated or unsaturated fluoroalkyl group; and X represents an aromatic ring or a heterocyclic group, a hydrocarbon group substituted with an aromatic ring or heterocyclic group, or an aromatic ring or heterocyclic group substituted with: a hydroxyl group, an amino group, a carboxyl group, a halogen atom, a hydrocarbon group, or an aromatic ring.

4. The recording medium according to claim 3, wherein said recording medium is a magnetic recording medium, and wherein said recording layer is a magnetic layer.

5. A non-fluorinated-alkyl compound being represented by the following formula (1) or (2):

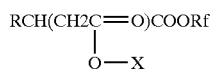
(1)
(2)

wherein R represents a saturated or unsaturated aliphatic hydrocarbon group having 6 to 30 carbon atoms; Rf represents a hydrocarbon group; and X represents an aromatic ring or a heterocyclic group, a hydrocarbon group substituted with an aromatic ring or heterocyclic group, or an aromatic ring or heterocyclic group substituted with: a hydroxyl group, an amino group, a carboxyl group, a halogen atom, a hydrocarbon group, or an aromatic ring.

6. A lubricant for recording medium, comprising a non-fluorinated-alkyl compound represented by the following formula (1) or (2):

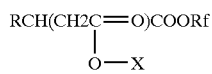
(1)
(2)

wherein R represents a saturated or unsaturated aliphatic hydrocarbon group having 6 to 30 carbon atoms; Rf represents a hydrocarbon group; and X represents an aromatic ring or a heterocyclic group, a hydrocarbon group substituted with an aromatic ring or heterocyclic group, or an aromatic ring or heterocyclic group substituted with: a hydroxyl group, an amino group, a carboxyl group, a halogen atom, a hydrocarbon group, or an aromatic ring.

7. A recording medium comprising a support, a recording layer, and a lubricant layer comprising a lubricant, wherein said recording layer and said lubricant layer are successively formed on said support, wherein said lubricant includes a non-fluorinated-alkyl compound represented by the following formula (1) or (2):

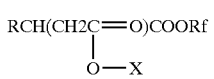
(1)
(2)

wherein R represents a saturated or unsaturated aliphatic hydrocarbon group having 6 to 30 carbon atoms; Rf represents a hydrocarbon group; and X represents an aromatic ring or a heterocyclic group, a hydrocarbon group substituted with an aromatic ring or heterocyclic group, or an aromatic ring or heterocyclic group substituted with: a hydroxyl group, an amino group, a carboxyl group, a halogen atom, a hydrocarbon group, or an aromatic ring.

* * * * *